United States Patent [19]
Schöning et al.

[11] Patent Number: 6,132,893
[45] Date of Patent: Oct. 17, 2000

[54] PH-SENSITIVE MICROSENSOR AND A METHOD OF MANUFACTURING A PH-SENSITIVE MICROSENSOR

[75] Inventors: Michael Josef Schöning, Jülich; Willi Zander, Aldenhoven; Jürgen Schubert, Elsdorf; Lutz Beckers, Köln; Axel Michael Schaub, Aachen; Peter Kordos, Jülich; Hans Lüth, Aachen, all of Germany

[73] Assignee: Forschungszentrum Jülich GmbH, Jülich, Germany

[21] Appl. No.: 08/999,569

[22] Filed: Dec. 3, 1997

Related U.S. Application Data

[63] Continuation-in-part of application No. PCT/DE96/01021, Jun. 4, 1996.

[30] Foreign Application Priority Data

Jun. 6, 1996 [DE] Germany .................. 195 20 059

[51] Int. Cl.[7] ................................................ B32B 9/00
[52] U.S. Cl. ................... 428/701; 428/34.4; 428/34.6; 428/172; 428/472; 428/702; 428/913; 204/403; 204/416; 204/418; 204/419
[58] Field of Search ............................ 428/701, 446, 428/447, 372, 198, 315.5, 913, 403, 172, 702, 472, 34.4, 34.6, 405; 204/403, 702, 416, 418, 419, 420, 426, 414, 415

[56] References Cited

U.S. PATENT DOCUMENTS

| 4,874,499 | 10/1989 | Smith et al. | 204/403 |
| 5,376,255 | 12/1994 | Gumbrecht et al. | 204/426 |
| 5,814,280 | 9/1998 | Tomita et al. | 422/82.01 |

Primary Examiner—Deborah Jones
Assistant Examiner—Abraham Bahta
Attorney, Agent, or Firm—Klaus J. Bach

[57] ABSTRACT

A pH sensitive microsensor which comprises a substrate on which a sensor membrane is formed by laser ablation of a target and depositing the target material on the substrate.

4 Claims, 1 Drawing Sheet

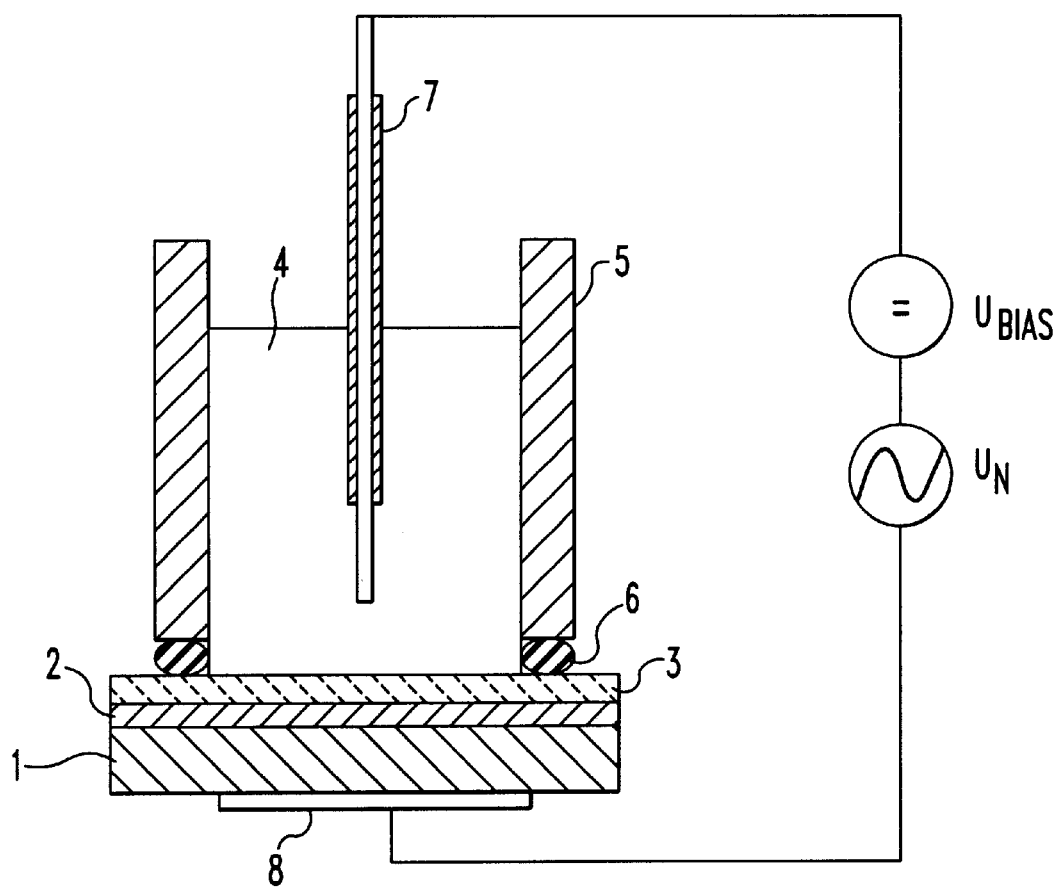

PH-SENSITIVE MICROSENSOR AND A METHOD OF MANUFACTURING A PH-SENSITIVE MICROSENSOR

This is continuation-in-part application of international application PCT/DE96/01021 filed Jun. 4, 1996 and claiming the priority of German applications 195 20 059.4 of Jun. 6, 1995 and 295 12 999.9 of Aug. 12, 1995.

BACKGROUND OF THE INVENTION

The invention resides in a pH-sensitive microsensor on silicon basis having a sensor membrane and in a method of making the microsensor.

The publications by T. Matsuro et al., "METHODS OF ISFET FABRICATION", Sensors and Actuators 1 (1981) p. 77, H. Abe et al., "ISFETs Using Inorganic Gate Thin Films", IEEE Trans. Electron. Dev. Ed. 26, 12 (1979, page 1939 or Bousse et al., Hysterisis in $Al_2O_3$-gate ISFETS, Sensors and Actuators B2 (1990) page 103, disclose silicon-based pH-sensitive microsensors.

These are so-called ion sensitive field effect transistors (ISFET), which, in their basic construction, correspond to a MOSFET. In place of the metallic gate electrode such a component includes a combination of a sensitive layer (sensor membrane), electrolyte and reference electrode. Furthermore, C. Cin et al., "An experimental study of inorganic gate ISFETS and Actuators B,1 (1990), p. 421, discloses that, instead of a complete ISFET, it is possible for example to use as pH-sensors also capacitive field effect structures, which, in their construction, correspond to the gate area of an ISFET.

In a pH-sensitive ISFET, this sensor membrane consists for example of $Si_3N_4$, $Ta_2O_5$ or also $Al_2O_3$. The best results with respect to sensitivity, stability, and selectivity were obtained for $Ta_2O_5$ and $Al_2O_3$.

The sensor membrane, particularly if $AL_2O_3$ is selected as the membrane material, is formed by sputter technology or by Chemical Vapor Deposition (CVD).

Microsensors, which include such sensor membranes have the disadvantage that they have relatively high drift rates.

It is therefore the object of the present invention to provide a sensor and a method of manufacturing such a sensor wherein the drift rate is reduced.

SUMMARY OF THE INVENTION

A pH sensitive microsensor comprises a substrate on which a sensitive layer is formed by laser ablation of a target and depositing the target material on the substrate.

It has been recognized that a pH-sensitive layer can be formed for capacitive field effect sensors on a semiconductor basis by $Al_2O_3$, deposition. The advantage of laser ablation resides in a simple process and in the controlled stoichiometric deposition of multi-component systems. In this process, preferably $AL_2O_3$ is used as the deposited material, but other materials can be used to form the membrane.

With laser ablation wherein, by means of the laser, material is taken out of a target and deposited on a surface to form the sensitive layer no expensive UHV technology is necessary as it is the case in a sputtering process, nor are there long pumping times or small growth rates. There is furthermore no need for the admission of special process gases ($AlCl_3$, $AlBr_3$, NO) nor for a complicated process gas supply and disposal as it is needed in connection with CVD deposition.

The microsensor has a high sensitivity in the area of, for example, 56 mV/pH for concentration ranges of pH=3 to pH=10. The microsensor has been found to be particularly advantageous with regard to long term stability while being exposed to an electrolyte. It has a stability of more than six months. Nevertheless, the sensor characteristics that is the sensor properties are essentially the same as those of the known sensors or they are even better.

Finally, with the use in sensors of sensitive layers, which were formed by laser ablation, the sensor drift rate has been found to be substantially smaller than with the sensors known in the art. While the sensors produced by sputter technology or CVD have a drift rate of at least 5 to 10 mV per day as it is known for example from IEEE Trans. On Electron Dev., Vol. Ed—26, No. 12, December 1979, pages 1939 ff. The sensor according to the invention has a drift rate of for example only 1.0 m Volt per day or better.

The microsensor according to the invention can be employed as chemical pH-sensor. However, on the basis of this sensor, a biochemical sensor having a a biosensitive component layer, particularly an enzyme layer, can be formed. Such a biosenstive sensor has the advantages mentioned above; it has especially also the low drift rates.

For a futher approximation to the ideal stoichiometry, the micro- or biosensor can be tempered during the manufacturing process in an oxygen atmosphere after the membrane is formed.

An embodiment of the invention will be explained below on the basis of the accompanying drawing.

BRIFF DESCRIPTION OF THE DRAWING

FIG. 1 shows a micro- or biosensor according to the invention.

DESCRIPTION OF A PREFERRED EMBODIMENT

FIG. 1 shows a micro or bin sensor comprising a substrate 1 of p-doped silicon (with a concentration of for example $5+10^{14}$ $p/cm^3$ and a substrate thickness of 400 $\mu m$), an insulating $SiO_2$ layer 2 (with a thickness of for example 30–100 nm) deposited on the substrate and a sensitive layer 3 of $Al_2O_3$ deposited on the insulating layer. if the sensor is to be a biosensor the layer 3 as shown in FIG. 1 is a sensor with a biosensitive layer which may consist for example of an enzyme.

A wall 5 is disposed on top of the sensitive layer 3 and sealed with respect to the sensitive layer 3 by an O-ring 6. A liquid electrolyte 4 is contained by the wall 5 on the sensitive layer 3. The liquid electrolyte has a pH value of for example pH=2 to pH=11 depending on the selected buffer solution. An AG-AgCl reference electrode 7 extends into the electrolyte and is connected, by way of the voltage source $V_{Bias}$ and an alternating voltage source $U_N$ with an aluminum contact electrode 8 (having a thickness of 200 nm) disposed on the backside of the substrate 1.

The thickness of the sensor membrane was selected to be in the range of 5 nm to 1000 nm particularly in the range of 30 nm to 100 nm.

The insulating layer 2 for forming the sensor membrane can be coated by laser-induced vaporization of an $Al_2O_3$ target using for example a KrF-laser. The deposition rate of the target material for forming the membrane is in the range of 0.01 nm/s to 10 nm/s, especially 1.0 nm/s. An oxygen partial pressure in the range of $1\times10^{-4}$ mbar to $1\times10^{-2}$ mBar was selected. The temperature at the substrate surface during the ablation was up to 1500° C.; it is more specifically in the range of 600° C. to 900° C., preferably 800° C.

The invention is not limited to the materials and dimensions as given herein. Other materials and dimensions could be utilized depending on the required limiting conditions. It is also conceivable to utilize multiple systems with several sensitive layers 3, particularly sensor layers and/or biosensitive components layers.

What is claimed is:

1. A pH sensitive microsensor comprising a substrate and a sensitive layer formed on said substrate by means of laser ablation wherein the microsensor has drift rate of only 1.0 mV.

2. A microsensor according to claim 1, wherein said microsensor membrane consists of $Al_2O_3$.

3. A microsensor according to claim 1, wherein a biosensitive layer is formed on said sensor membrane.

4. A microsensor according to claim 3, wherein said biosensitive component layer consists of an enzyme.

* * * * *